United States Patent
Guala

(10) Patent No.: US 7,556,060 B2
(45) Date of Patent: Jul. 7, 2009

(54) FLOW COMPONENT FOR MEDICAL INFUSION / TRANSFUSION LINES

(75) Inventor: Gianni Guala, Turin (IT)

(73) Assignee: Industrie Borla S.p.A., Moncalieri (Turin) (IT)

( * ) Notice: Subject to any disclaimer, the term of this patent is extended or adjusted under 35 U.S.C. 154(b) by 331 days.

(21) Appl. No.: 11/285,373

(22) Filed: Nov. 22, 2005

(65) Prior Publication Data

US 2006/0108008 A1 May 25, 2006

(30) Foreign Application Priority Data

Nov. 24, 2004 (IT) .......................... TO2004A0830

(51) Int. Cl.
G05D 11/03 (2006.01)

(52) U.S. Cl. .............................. 137/599.03; 137/599.12; 137/895

(58) Field of Classification Search ................. 137/605, 137/895, 896, 599.03, 205.5, 599.12; 604/31, 604/83

See application file for complete search history.

(56) References Cited

U.S. PATENT DOCUMENTS

| | | | |
|---|---|---|---|
| 2,953,160 A * | 9/1960 | Brazier ................... | 137/599.12 |
| 3,150,676 A * | 9/1964 | Robinson .................... | 137/896 |
| 3,188,055 A * | 6/1965 | Lutjens et al. ......... | 137/599.01 |
| 3,194,444 A * | 7/1965 | Hubert ..................... | 137/205.5 |
| 3,810,787 A * | 5/1974 | Yoeli et al. ..................... | 134/29 |
| 3,941,211 A * | 3/1976 | Grutter et al. ............ | 137/205.5 |
| 4,246,932 A * | 1/1981 | Raines ........................ | 137/512 |
| 4,819,684 A * | 4/1989 | Zaugg et al. ................... | 604/83 |
| 4,915,687 A * | 4/1990 | Sivert .......................... | 604/83 |
| 5,221,271 A | 6/1993 | Nicholson et al. ........... | 604/283 |
| 5,306,265 A | 4/1994 | Ragazzi ...................... | 604/283 |
| 5,618,268 A | 4/1997 | Raines et al. ................ | 604/82 |
| 6,042,341 A | 3/2000 | Richter ....................... | 417/151 |
| 6,390,120 B1 * | 5/2002 | Guala .................... | 137/512.15 |
| 2003/0015897 A1 | 8/2003 | Russo ........................ | 604/537 |

OTHER PUBLICATIONS

European Search Report for EP 05 11 1082, Mar. 14, 2006.

* cited by examiner

Primary Examiner—Stephen M Hepperle
(74) Attorney, Agent, or Firm—Heslin Rothenberg Farley & Mesiti P.C.; Victor A. Cardona

(57) ABSTRACT

A flow component for medical infusion/transfusion lines comprises a main duct and a lateral tubular connection containing a one-way valve, in an area corresponding to which the main duct has an axial section with a wall having a convergent-divergent profile.

13 Claims, 1 Drawing Sheet

FLOW COMPONENT FOR MEDICAL INFUSION / TRANSFUSION LINES

CROSS REFERENCE TO RELATED APPLICATIONS

This application is a claims priority from Italian patent application No. TO2004A000830, filed on Nov. 24, 2004, the entire disclosure of which is incorporated herein by reference.

FIELD OF THE INVENTION

The present invention relates in general to medical infusion/transfusion lines.

More in particular, the subject of the invention is a flow component for such medical lines that comprises a main duct having a lateral tubular connection communicating with the main duct through a one-way valve to enable introduction of a secondary liquid within said main duct.

STATE OF THE PRIOR ART

In the above flow components, between the one-way valve, typically including an elastic-diaphragm open-close element, and the main duct there remains an albeit restricted space that gives rise to a dead space, within which part of the secondary liquid introduced from the lateral connection and also air may stagnate.

SUMMARY OF THE INVENTION

The object of the present invention is to overcome said drawback in a particularly simple and functional way.

According to the invention, this object is achieved thanks to the fact that the aforesaid main duct has, in an area corresponding to the one-way valve, an axial section with a wall having a convergent-divergent profile.

Thanks to this idea of solution the main duct, in practice made basically as a venturi tube in the area of the lateral connection, produces in use the effect of an ejector, thanks to which the kinetic energy possessed by the flow of the liquid within the main duct itself is partially transferred to the dead space situated immediately downstream of the one-way valve, eliminating the stagnation of the secondary liquid introduced into the lateral connection and of air.

From the European patent EP-B-1099457, filed in the name of the present applicant, a one-way valve is known, the open-close element of which consists of an elastic diaphragm housed within a chamber and normally set in hermetic contact against an annular valve seat. With such a configuration, the invention envisages that said chamber is comprised between the main duct and the lateral connection and communicates with the aforesaid axial section with a wall having a convergent-divergent profile of the main duct through a first passage located in an area corresponding to the convergent profile and a second passage located in an area corresponding to the divergent profile of said wall.

With said arrangement, in use the flow of liquid within the main duct, accelerated by the convergent profile, penetrates within the chamber through the first passage and comes out through the second passage, thus not only preventing any stagnation within the duct but also performing an action of continuous flushing.

According to a preferred embodiment of the invention, the axial section with a wall having a convergent-divergent profile is defined by a localized restriction of the aforesaid main duct.

BRIEF DESCRIPTION OF THE DRAWINGS

The invention will now be described in detail with reference to the annexed plate of drawings, which are provided purely by way of non-limiting example and in which.

DETAILED DESCRIPTION OF THE INVENTION

Figure 1:
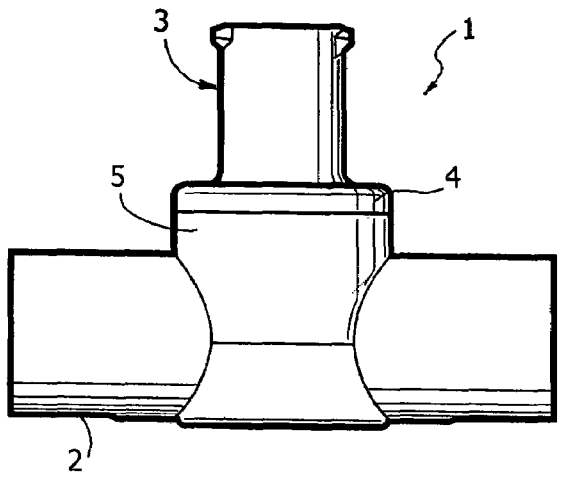
FIG. 1 is a schematic view in side elevation of a flow component according to the invention for medical infusion/transfusion lines.
Figure 2:
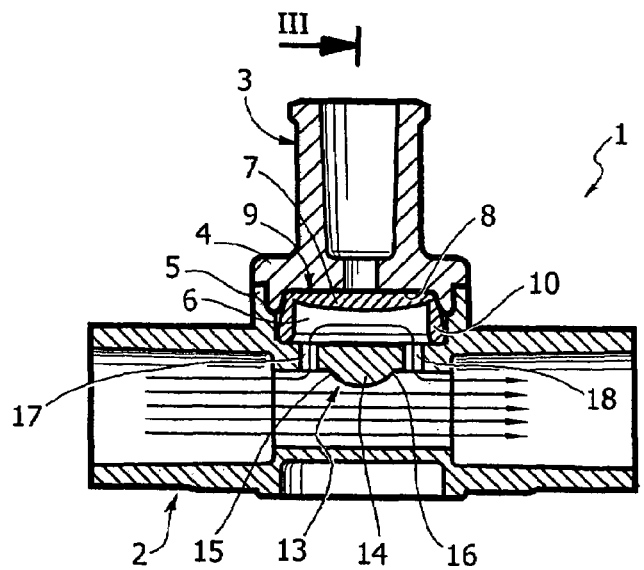
FIG. 2 is a longitudinal cross-sectional view of the component of FIG. 1.

Designated as a whole by 1 in the plate of drawings is a flow component according to the invention that can be applied to a medical infusion/transfusion line, basically comprising a main duct 2, designed in use to be traversed by a flow of a primary liquid in the direction indicated by the arrows in FIG. 2, and a lateral tubular connection 3 directed at right angles to the duct 2 for introduction of a secondary liquid within it.

The lateral connection 3 is shaped, in the case of the example illustrated, like a female luer-lock connector, the internal end of which has an annular flange 4, seal-fixed in an area corresponding to an annular collar 5 projecting laterally from the duct 2.

Figure 3:
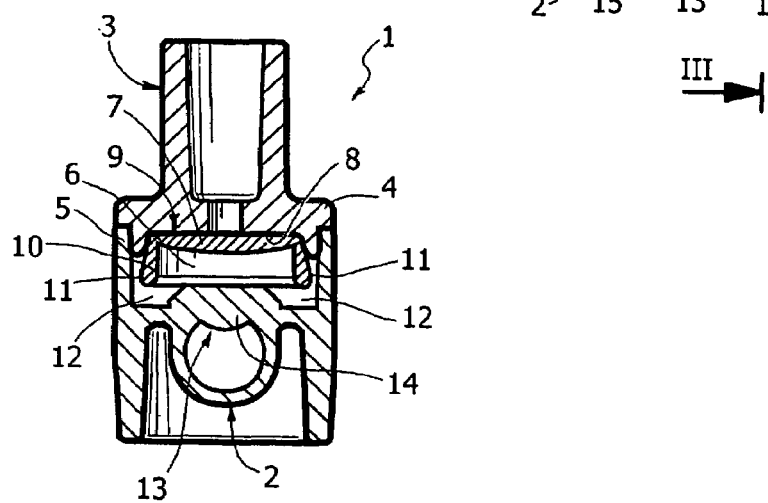
FIG. 3 is a transverse cross-sectional view according to the line III-III of the component of FIG. 2.

Defined between the annular flange 4 and the annular collar 5 is a chamber 6 for a one-way valve, which comprises, in the case of the example illustrated, an elastic diaphragm 7, normally set in hermetic contact against an annular valve seat 8 of the lateral connection 3. The general conformation of the one-way valve, and in particular of the diaphragm 7, corresponds to the one described and illustrated in the already cited European patent No. EP-B-1099457. More specifically, the diaphragm 7 is constituted by the bottom wall of a cup-shaped element 9, made by means of injection moulding of liquid silicone, the side wall 10 of which rests on the bottom of the chamber 6 and tends to press the diaphragm 7 in sealing contact against the annular valve seat 8. An overpressure generated within the lateral connection 3 as a result of the introduction of a secondary liquid within it, produces deflection of the diaphragm 7 and thus opening of the one-way valve, enabling the passage of the secondary liquid from the lateral connection to the chamber 6 and then to the main duct 2, through axial passages 11 and radial passages 12 (FIG. 3).

According to the invention, the main duct 2 has, in an area corresponding to the chamber 6, an axial section 13 with a wall having a convergent-divergent profile. Said axial section 13 is advantageously defined by a localized restriction of rounded shape 14 of the wall of the duct 2, defined upstream of which (with respect to the direction of flow of the primary liquid within said duct 2) is the convergent profile 15, and defined downstream of which is the divergent profile 16.

The convergent profile 15 communicates with the chamber 6 through a first passage 17, and the divergent profile 16 communicates with said chamber 6 through a second passage 18.

In use, the section 13 with a wall having a convergent-divergent profile 15, 16 defines a venturi tube designed to prevent the stagnation of liquid and air within the chamber 6 of the one-way valve 7, 8. Part of the flow of the primary liquid within the duct 2 penetrates into the chamber 6 through the first passage 17 and comes out from this through the second passage 18, drawn along thanks to the ejector effect obtained by said flow of the primary liquid in an area corresponding to the divergent profile 16. In this way the primary liquid in the main duct 2 not only brings about an effect of emptying of the chamber 6, but also an effective action of continuous flushing.

The example of embodiment described with reference to the plate of drawings constitutes only one of the possible applications of the invention: it may, in fact, be to equal advantage applied also to flow components equipped with one-way valves having an arrangement different from the one described, in particular as regards the configuration of its open-close element, which may, for example, consist of a simple, generally plane, elastic membrane, or of a different element.

What is claimed is:

1. A flow component for medical infusion/transfusion lines comprising:
    a main duct connected to a lateral tubular connection communicating with the main duct through a one-way valve to enable introduction of a secondary liquid into said main duct;
    said main duct comprising an axial connecting section where said lateral connection is connected to said main duct, said axial connecting section having a wall comprising an inside surface having a protrusion forming a reduced cross-sectional area in a connecting section relative to a remainder of said main duct, said protrusion forming a convergent-divergent profile along said inside surface, said profile defining a venturi tube;
    a first passage located in a converging portion of said convergent-divergent profile and a second passage located in a diverging portion of said convergent-divergent profile;
    said first passage and said second passage extending from said main duct through said wall to a chamber of said one-way valve such that said main duct, said first passage, said chamber and said second passage are in fluid communication with each other to define a second flow path of a primary liquid from said main duct through said first passage, through said chamber, through said second passage and back to said main duct, said second flow path avoiding passing through said venturi tube;
    said chamber arranged between said main duct and said lateral connection on an outer side of said wall at said axial connecting section, said inside surface of said wall defining a first flow path of the primary liquid passing through said venturi tube;
    wherein said one-way valve includes an elastic-diaphragm open-close element housed within said chamber and normally set in hermetic contact against an annular valve seat of said lateral connection, said elastic diaphragm being movable away from said valve seat following application of an overpressure within said lateral connection to open communication between said lateral connection and said main duct through said chamber and at least one of said first passageway and said second passageway; and
    wherein said chamber is bounded by said elastic-diaphragm and an outside surface of said main duct.

2. The flow component according to claim 1, wherein said section having a convergent-divergent profile is defined by a localized restriction of said main duct.

3. The flow component according to claim 2, wherein said localized restriction is rounded.

4. The flow component according to claim 1, wherein said section having a convergent-divergent profile is defined by a localized restriction of said main duct.

5. The flow component of claim 1, wherein said one-way valve avoids bounding said first passage and said second passage.

6. The component of claim 1, wherein said first passage and said second passage are separate from said annular valve seat.

7. The flow component of claim 1, wherein said valve seat is spaced from said wall.

8. The flow component of claim 1, wherein said valve seat is spaced from said outer side of said wall.

9. The flow component of claim 1, wherein said first passage and said second passage are aligned substantially parallel to said lateral tubular connection.

10. The flow component of claim 1, wherein said first passage and said second passage are separated from said valve seat by said chamber.

11. The flow component of claim 1, wherein said diaphragm avoids bounding said first passage and said second passage.

12. The flow component of claim 1, wherein said first passage and said second passage are completely longitudinally bounded by said wall.

13. The flow component of claim 1, wherein said second flow path extends radially outside said protrusion relative to an axis of said main duct.

* * * * *